United States Patent [19]

Bodart

[11] 4,266,877
[45] May 12, 1981

[54] PHOTOMETER WITH INTERCHANGEABLE CALIBRATION CARDS

[75] Inventor: Detlef Bodart, Darmstadt, Fed. Rep. of Germany

[73] Assignee: Merck Patent Gesellschaft mit beschränkter Haftung, Darmstadt, Fed. Rep. of Germany

[21] Appl. No.: 70,077

[22] Filed: Aug. 27, 1979

[30] Foreign Application Priority Data

Aug. 28, 1978 [DE] Fed. Rep. of Germany ....... 2837443

[51] Int. Cl.³ .......................... G01J 3/50; G01N 21/31
[52] U.S. Cl. .................................. 356/414; 324/115; 356/418; 356/419
[58] Field of Search .............. 356/409, 414, 416, 418, 356/419; 324/115

[56] References Cited

U.S. PATENT DOCUMENTS 3,594,086  7/1971  Hughes et al. ..................... 356/416
3,736,433  5/1973  Davis et al. ........................ 356/414

Primary Examiner—Vincent P. McGraw
Attorney, Agent, or Firm—Millen & WHite

[57] ABSTRACT

A photometer adapted for use with interchangeable calibration cards, comprising a galvanometer having a transparent cover over its indicator needle, the cover being provided with a slot along its edge which faces the center of the photometer, the slot being adapted to permit insertion of one end of one of the calibration cards into the covering, beneath the needle; a zone adjacent the galvanometer and the slot containing an orifice adapted to receive a photometer cell, a first control knob located on a side of the photometer for setting the photometer to its blank value; and a second control knob, for adjusting the wavelength of the photometer, having coded means thereon for corrolating various wavelengths of the photometer, produced by rotating the second control knob to various settings, to data contained on the calibration cards.

10 Claims, 2 Drawing Figures

PHOTOMETER WITH INTERCHANGEABLE CALIBRATION CARDS

BACKGROUND OF THE INVENTION

This invention relates to a photometer with interchangeable calibration cards, more particularly one consisting essentially of a galvanometer and a zone containing an orifice for a cell.

In colorimetry, one of the analytical procedures very commonly used in chemical analysis, the substances to be measured in solution are converted, by the addition of a reagent, into color compounds. From the resultant color intensity, concentration of the substance in the solution can be derived. Instruments used to measure color intensity are photoelectric colorimeters or spectrophotometers. In certain fields of analysis, photometers with interchangeable scales calibrated direct in concentrations are used. Each calibration scale is suited to a specific method of measurement, for which there is frequently a ready-for-use reagent kit. In each case, however, a number of parameters must be fixed before carrying out a measurement on the photometer. In the case of a colorimeter of simple construction, these parameters are, for example, the choice of the appropriate wavelength, the choice of the size of cell and the setting of the apparatus to the so-called zero extinction., viz., setting to the blank value. In actual practice, one of these parameters is frequently set incorrectly. For example, the wavelength from the preceding determination may not be changed or incorrect instructions, which are not suited to the calibration scale, are erroneously selected.

OBJECTS OF THE INVENTION

Accordingly, an object of the invention is the provision of a novel photometer, the use of which can substantially avoid such errors. Other objects will be apparent to those skilled in the art to which this invention pertains.

SUMMARY OF THE INVENTION

According to this invention, there is provided a photometer with interchangeable calibration cards, having, as three zones arranged successively, a galvanometer zone, a zone which contains the orifice for a cell and a zone which serves as the supporting base for the calibration scales.

DESCRIPTION OF THE DRAWINGS

With reference to the drawings, which are perspective views respectively, of a preferred embodiment of the photometer of this invention and of the calibration card employed therewith:

As shown in FIG. 1, the preferred photometer 1 is essentially a narrow rectangular desk, the length of which is greater than the width, consisting generally of first 2 and second 3 end zones and a central zone 4, having upper faces 5, 7 and 9, respectively. Mounted on the upper face 5 of the first zone 2 is a galvanometer 11 having a dual compartmented flat rectangular transparent cover 13, consisting of a thin upper closed compartment 15, providing a housing for a galvanometer indicator needle 17, and positioned over a corresponding thin lower compartment 19 whose side 21, which faces center zone 4 of photometer 1, is open along its length in the form of a slot, thereby forming a recess in said cover 13 to permit the insertion into lower compartment 19 of one end of a calibration card 50. Center zone 4 contains a centrally positioned orifice 23 into which a sample cell 70 can be inserted. A pair of control knobs 25,27 are mounted on opposite vertical sides of the central zone 4 of photometer 1. The diameters of the control knobs 25,27 are such that the uppermost peripheral surface 29,31 of each is approximately the same height as the upper face 9 of central zone 4. Mounted on the upper face 7 of the second end or supporting zone 3 are a pair of positioning studs 33,35.

As shown in FIG. 2, the calibration card 50 used in conjunction with photometer 1, has a scale 51, indicated in FIG. 2 as a curved line for galvanometer 11 on the end 53 thereof which is inserted into open side 21 of lower compartment 19. A larger hole 55 of a size to accommodate cell 70 is positioned in the central portion 57 of card 50 so as to be positioned axially in line with orifice 23 when card 50 is mounted on photometer 1 with one end 53 thereof inserted in lower compartment 19 of cover 13. A pair of smaller holes 59,61 are positioned on the end 63 of card 50 opposite the end 53 bearing the galvanometer scale 51, to permit insertion of the positioning pins 33,35 therethrough.

Figure 1:
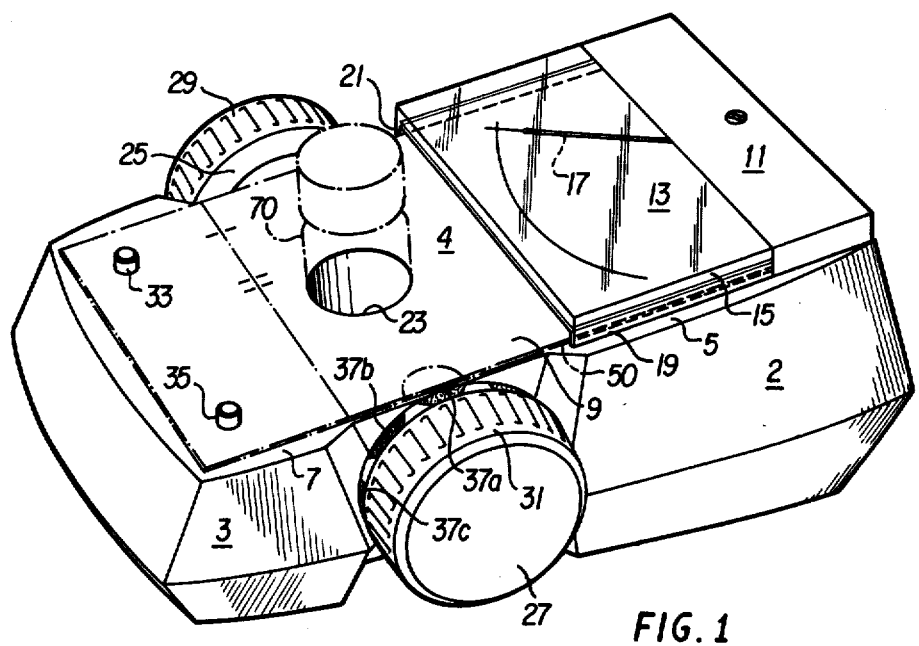
FIG. 1 is an overall perspective view of the top, one end and one side of the photometer with a calibration card and a sample cell, both shown in phantom, mounted thereon.
Figure 2:
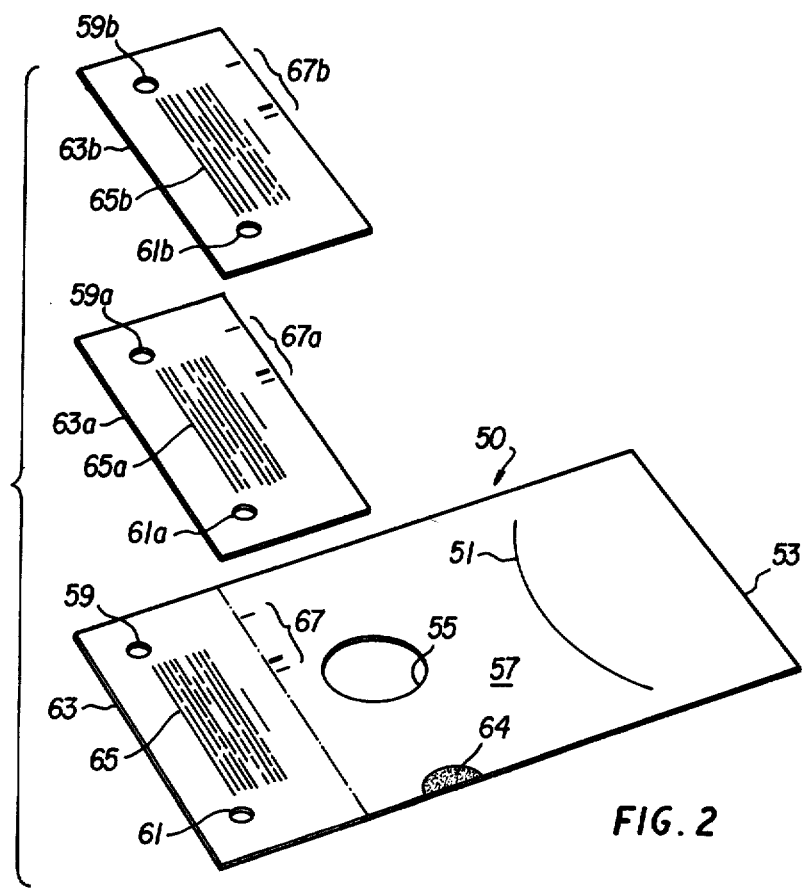
FIG. 2 is a perspective top view of a calibration card shown in FIG. 1 mounted on the photometer, and a plurality of instruction sheets for use therewith.

The upper third of the calibration card 50, which preferably is oblong in shape and about DIN A 6 in size, is provided with the scale 51, which can be read off in concentration units. The use of smaller cells in cards with a large punched hole is prevented by an annular warning marker (not shown), which forms part of the necessary reduction insert, becoming visible. This reduction insert consists e.g. of a plastic tube with a red colored annular sleeve on the top as a warning marker.

Control knob 25 is used to set photometer 1 at its blank value (zero point alignment). It is preferably located on that side of the photometer on which the indicator needle 17 has the corresponding stop. This is indicated, for example, on the calibration card by a line (not shown) between knob 25 and the stop for the indicator needle 17 (zero point of the scale). The second control knob 27 on the opposite side of the photometer, is used to adjust the wavelength. In the case of relatively simple equipment, this is a multistage switch, with which corresponding colored or interference glass filters are brought into the path of the rays. The absorption maximum of the filter is indicated by differing colored areas 37a, 37b, 37c on the peripheral surface of control knob 27, which color is approximately complementary to that of the filter, i.e., approximately corresponds to that of the measurement solution. The code color or marking of the filter specified for the measurement is at the same time given on the adjacent surface 64 of the calibration card 50 so that measurements with an incorrect filter setting are virtually precluded. In the lower third 63 of the card 50 are a pair of small positioning holes 59,61, which, by fitting over corresponding position studs 33,35, ensure that the card is accurately positioned on the photometer. Brief instructions 65 for use are printed at this end of the calibration card 50. The portion 63 of card 50 bearing these instructions can be covered by a smaller instruction card 63a, 63b giving the same instructions in a foreign language 65a, 65b, which smaller card is similarly positioned over the calibration card 50 by a pair of holes 59a, 61a; 59b, 61b, adapted to be fitted over the positioning studs 33,35. A series of coding lines 67 on the calibration card 50 and a corresponding matching series of coding lines 67a, 67b on the instruction cards 63a, 63b, prevents a foreign language instruction card which does not correspond to the calibration card positioned on the photometer from erroneously being placed on top of calibration card. The location and the size of the positioning holes preferably correspond to the spacing and the diameter of the holes which are obtained with conventional punches. The size of the calibration cards 50 preferably corresponds to the conventional size for ring files, so that all of the cards can be stored as a collection, for example in a DIN A 6 ring file.

In carrying out an analysis, the calibration card 50 required for the analysis is first inserted, by the leading edge of the upper third portion 53 thereof through the slot opening 21 in the photometer cover 13 until positioning holes 59,61 are aligned with the positioning studs 33,35 of the supporting zone 3, thereby ensuring accurate mounting of the card on the photometer. If a foreign language instruction card 63a or 63b is employed, it is then mounted over calibration card 50 by placing the former on studs 33,35 through the matching small holes 59a, 61a or 59b, 61b. The wavelength of the photometer is adjusted to the correct value by turning knob 27 until it is in a position in which the correct code color zone 37a, 37b or 37c on the knob is aligned with the corresponding color marking 64 on the calibration card 50 which is directly adjacent thereto. A cell 70 containing the correct blank is then inserted through the larger hole 55 in card 50 and into the orifice 23 provided therefor in the photometer. The galvanometer 11 is adjusted with control knob 25 to the zero point as shown by needle 17. The blank cell 70 is then replaced by a like cell 70 containing the sample to be examined and the concentration of the particular substance therein is read off directly from the calibration scale 51.

In principle, all substances which either enter into a color reaction or absorb in the UV range on the addition of the reagent, can be determined in this manner. Examples of determinations which can thus be carried out are the diagnostically important quantitative determination of the constituents of body fluids, for example, glucose, cholesterol, urea, uric acid, protein, triglycerides and the like, pH value determinations or the determination of the concentrations of specific cations and anions in water samples and aqueous digestion solutions.

By the use of the photometer of this invention and the interchangeable calibration scales employed therewith, which contain all of the data necessary for the accurate determination of correct values, it is possible to avoid the errors which constantly arise in practice and which result from incorrect setting of the equipment.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A photometer adapted for use with interchangeable calibration cards, comprising a galvanometer having a transparent cover over its indicator needle, said cover being provided with a slot along its edge which faces the center of said photometer, said slot being adapted to permit insertion of one end of one of said calibration cards into said covering, beneath said needle; a zone adjacent said galvanometer and said slot containing an orifice adapted to receive a photometer cell, a first control knob located on a side of said photometer for setting the photometer to its blank value; and a second control knob, for adjusting the wavelength of the photometer, having coded means thereon for corrolating various wavelengths of said photometer, produced by rotating said second control knob to various settings, to data contained on said calibration cards.

2. A photometer according to claim 1, wherein said coded means on said second knob are positioned along the peripheryl edge thereof and the uppermost portion of said peripheryl edge is at approximately the same height as the upper face of said orifice-containing zone.

3. A photometer according to claim 1, wherein said cover comprises an upper closed compartment housing the galvanometer needle and a lower compartment having said slot in its edge facing the center of the photometer and forming a recess adapted to receive the portion of the calibration card inserted in said cover.

4. A photometer according to claim 1 having a second zone adjacent to said orifice-containing zone, adapted to serve as a supporting base for one end of said calibration cards and having positioning means thereon for positioning one of said cards on said photometer.

5. A photometer according to claim 2 wherein said positioning means comprises at least one stud projecting upwardly from the face of said second zone.

6. A photometer according to claim 1, adapted to have mounted thereon a calibration card of a size approximately corresponding to the surface area of the top face of said photometer.

7. A photometer according to claim 1, having a second zone, adjacent to said orifice-containing zone, adapted to serve as a supporting base for the end of one of said calibration cards which is opposite to the end thereof which is inserted in said cover, said second zone having a pair of positioning studs mounted thereon for positioning one of said cards on said photometer; and wherein said coded means on said second knob are positioned along the peripheryl edge thereof and the uppermost portion of said peripheryl edge is at approximately the same height as the upper face of said orifice-containing zone; and wherein said cover comprises an upper closed compartment housing the galvanometer needle and a lower compartment having said slot in its edge facing the center of the photometer and forming a recess adapted to receive the portion of the calibration card inserted in said cover.

8. In combination, a photometer according to claim 5 and a calibration card adapted to be mounted on the top face of said photometer, said card having a larger hole therein centrally positioned so as to be axially aligned with said orifice in said photometer, thereby permitting a cell to be inserted in said orifice, and one or more smaller corresponding in number to the number of said studs and positioned so that said stubs project therethrough when said card is mounted on the face of said photometer.

9. A combination according to claim 8, wherein said coded means on said second knob are positioned along the peripheryl edge thereof and the uppermost portion of said peripheryl edge is at approximately the same height as the upper face of said orifice-containing zone, and wherein said cover comprises an upper closed compartment housing the galvanometer needle and a lower compartment having said slot in its edge facing the center of the photometer and forming a recess adapted to receive the portion of the calibration card inserted in said cover.

10. A combination according to claim 8, further comprising an instruction sheet having one or more small holes corresponding in number to said studs and positioned so that said studs project therethrough when said sheet is mounted on the face of said photometer, said sheet being of a size which covers only said second zone of said photometer.

* * * * *